US006306098B1

(12) United States Patent
Orr et al.

(10) Patent No.: US 6,306,098 B1
(45) Date of Patent: Oct. 23, 2001

(54) APPARATUS AND METHOD FOR NON-INVASIVELY MEASURING CARDIAC OUTPUT

(75) Inventors: Joseph A. Orr; Scott A. Kofoed; Dwayne Westenskow, all of Salt Lake City, UT (US); Michael B. Jaffe, Cheshire, CT (US)

(73) Assignee: Novametrix Medical Systems Inc., Wallingford, CT (US)

( * ) Notice: Subject to any disclaimer, the term of this patent is extended or adjusted under 35 U.S.C. 154(b) by 0 days.

(21) Appl. No.: 08/770,138

(22) Filed: Dec. 19, 1996

(51) Int. Cl.$^7$ .................................................... A61B 15/00

(52) U.S. Cl. ...................... 600/526; 600/481; 128/200.26

(58) Field of Search ......................... 128/200.26, 207.14, 128/207.15, 207.16; 600/483, 484, 485, 532, 529, 531, 543, 481, 526

(56) References Cited

U.S. PATENT DOCUMENTS

| 4,192,301 | 3/1980 | Hardwick . |
| 4,239,038 | 12/1980 | Holmes . |
| 4,941,476 | 7/1990 | Fisher . |
| 4,947,860 | 8/1990 | Fisher . |
| 5,299,579 | 4/1994 | Gedeon et al. . |

FOREIGN PATENT DOCUMENTS

WO 98/12963    4/1998  (WO) .

OTHER PUBLICATIONS

Sackner, Marvin A., *Measurement of cardiac output by alveolar gas exchange*, Handbook of Physiology~ The Respiratory System IV, Chapter 13: Pulmonary Capillary Blood Flow, pp. 233–255.

de Abreu, M. Gama, et al., *Realiability of the Partial $CO_2$ Rebreathing Technique for Measurement of Cardiac Output*, Proceedings RC IEEE–EMBS & 14th BMESI–1995 (3 pages).

de Abreu, Marcel Gama, et al., *Partial carbon dioxide breathing: A reliable technique for noninvasive measurement of nonshunted pulmonary capilary blood flow*, Crit Care Med 1997, vol. 25, No. 4, pp. 675–683.

Osterlund, B., et al., *A new method of using gas exchange measurements for the noninvasive determination of cardiac output: clinical experiences in adults following cardiac surgey*, Acta Anaesthesiologica Scandinavica 39 (1995), pp. 727–732.

Gedeon, A., et al., *Noninvasive Cardiac Output Determined with a New Method Based on Gas Exchange Measurements and Carbon Dioxide Rebreathing: A Study in Animals/Pigs*, Journal of Clinical Monitoring, vol. 8, No. 4, Oct. 1992, pp. 267–278.

Gedeon, A., et al., *A new method for nonivasive bedside determination of pulmonary blood flow*, Medical & Biological Engineering & Computing, Jul. 1980, pp. 411–418.

(List continued on next page.)

*Primary Examiner*—Robert L. Nasser
(74) *Attorney, Agent, or Firm*—Trask Britt

(57) ABSTRACT

Apparatus and methods for non-invasively determining cardiac output using partial re-breathing techniques are disclosed in which the apparatus is constructed with an instantaneously adjustable deadspace for accommodating differences in breathing capacities of various patients. The apparatus is constructed of inexpensive elements, including a single two-way valve which renders the apparatus very simple to use and inexpensive so that the unit may be readily disposable. The method of the invention provides a novel means of estimating cardiac output based on alveolar $CO_2$ values rather than end-tidal $CO_2$ values as previously practiced. A program for calculating cardiac output is also disclosed.

26 Claims, 12 Drawing Sheets

OTHER PUBLICATIONS de Abreu, Marcelo Gama, et al., *Measurement of Pulmonary Capillary Blood Flow for Trending Mixed Venous Blood Oxygen Saturation and Oxygen Delivery*, 1 page.

Winkler, Tilo, et al., *Pulmonary Capillary Blood Flow by Partial $CO_2$ Rebreathing: A Simulation Study Using a Biocompartmental Model of Gas Exchange*, 1 page.

de Abreu, Marcelo Gama, et al., *Is the Partial $CO_2$ Rebreathing Technique a Useful Tool for Trending Pulmonary Capillary Blood Flow During Adjustments of Peep?*, 1 page.

Article entitled "Noninvasive Measurement of Cardiac Output Using Partial $CO_2$ Rebreathing" by John M. Capek and Rob J. Roy (pp. 653–661)–Printed in IEEE Transactions On Biomedical Engineering, vol. 35, No. 9 –Sep. 1988.

Article entitled "Noninvasive Measurement of Cariac Output Using Partial Carbon–Dioxide Rebreathing" by John Michael Capek (title, introductory pages and pp. 127–132) –Printed by UMI Dissertation Services –Dec. 1988.

Article entitled "Noninvasive Pulmonary Blood Flow for Optimal Peep" by A. Gedeon, ICOR AB, Ulvsundavägen 178 B, S–161 30 Bromma, Sweden (pp. 49–58).

Article entitled "Non–invasive pulmonary blood flow measurement by means of $CO_2$ analysis of expiratory gases" by Bosman, R.J., et al., Intesive Care Med (1991) 17:98–102.

Abstract FC 11 of article entitled "a Non–Invasive Technique for Measurement of Lung Perfusion" by H. Blomquist et al., published in "Monitoring, Computer, Instrumentation", Intensive Care Medicine (1986) 12:172.-

APPARATUS AND METHOD FOR NON-INVASIVELY MEASURING CARDIAC OUTPUT

BACKGROUND

1. Field of the Invention

This invention relates to non-invasive means of determining cardiac output in patients, and specifically relates to partial re-breathing systems and methods for determining cardiac output in patients.

2. Statement of the Art

It is important in many medical procedures to determine or monitor the cardiac output of a patient. Techniques are known and used in the art which employ the use of catheters inserted at certain arterial points (e.g., femoral artery, jugular vein, etc.) to monitor blood temperature and pressure in order to determine cardiac output of the patient. Although such techniques can produce a reasonably accurate result, the invasive nature of the procedure has high potential for morbidity and mortality consequences.

Adolph Fick's measurement of cardiac output, first proposed in 1870, has served as the standard by which all other means of determining cardiac output have been evaluated since that date. Fick's well-known equation, written for $CO_2$, is:

$$Q = \frac{V_{CO_2}}{\left(C_{vCO_2} - C_{aCO_2}\right)}$$

where Q is cardiac output, $V_{CO_2}$ is the amount of $CO_2$ excreted by the lungs and $$C_{aCO_2} \text{ and } C_{vCO_2}$$

are the arterial and venous $CO_2$ concentrations, respectively. Notably, the Fick Equation presumes an invasive method (i.e., catheterization) of calculating cardiac output because the arterial and mixed venous blood must be sampled in order to determine arterial and venous $CO_2$ concentrations.

It has previously been shown, however, that non-invasive means may be used for determining cardiac output while still using principles embodied in the Fick Equation. That is, expired $CO_2$ ("p$CO_2$") levels can be monitored to estimate arterial $CO_2$ concentrations and a varied form of the Fick Equation can be applied to evaluate observed changes in p$CO_2$ to estimate cardiac output. One use of the Fick Equation to determine cardiac output in non-invasive procedures requires the comparison of a "standard" ventilation event to a sudden change in ventilation which causes a change in expired $CO_2$ values and a change in excreted volume of $CO_2$. The commonly practiced means of providing a sudden change in effective ventilation is to cause the ventilated patient to re-breath a specified amount of previously exhaled air. This technique has commonly been called "re-breathing."

Prior methods of re-breathing have used the partial pressure of end-tidal $CO_2$ to approximate arterial $CO_2$ while the lungs act as a tonometer to measure venous $CO_2$. That method of re-breathing has not proven to be a satisfactory means of measuring cardiac output because the patient is required to breath directly into and from a closed volume in order to produce the necessary effect. However, it is usually impossible for sedated or unconscious patients to actively participate in inhaling and exhaling into a bag. The work of some researchers demonstrated that the Fick Equation could be further modified to eliminate the need to directly calculate venous $P_{CO_2}$ ($P_{vCO_2}$) by assuming that the $P_{vCO_2}$ does not change within the time period of the perturbation, an assumption that could be made by employing the partial re-breathing method. (See, Capek et al., "Noninvasive Measurement of Cardiac Output Using Partial $CO_2$ Rebreathing", *IEEE Transactions On Biomedical Engineering*, Vol. 35, No. 9, September 1988, pp. 653–661.)

Known partial re-breathing methods are advantageous over invasive measuring techniques because they 1) are non-invasive, 2) use the accepted Fick principle of calculation, 3) are easily automated, 4) require no patient cooperation and 5) allow cardiac output to be calculated from commonly monitored clinical signals. However, known partial re-breathing methods have significant disadvantages as well. Specifically, known methods 1) are less accurate with non-intubated or spontaneously breathing patients, 2) only allow intermittent measurements (usually about every four minutes), 3) result in an observed slight, but generally clinically insignificant, increase in arterial $CO_2$ levels and 4) do not permit measurement of shunted blood flow (that is, blood which does not participate in gas exchange). Further, known apparatus used for partial re-breathing techniques are of standard construction and do not compensate for differences in patient size or capacities. In addition, many devices employ expensive elements such as three-way valves, which render the devices too expensive to be used as disposable units.

Thus, it would be advantageous to provide a means of measuring cardiac output using partial re-breathing techniques which 1) overcome the disadvantages of prior systems, 2) provide better and more continuous measurement, and 3) require less expensive equipment, thereby making the device suitable for manufacturing as a single-use, or disposable, product. It would also be advantageous to provide partial re-breathing apparatus which is instantaneously adjustable to compensate for various sizes and capacities of patients. Further, it would be advantageous to provide new methods of estimating cardiac output based on alveolar $CO_2$ output rather than end-tidal $CO_2$ as is currently used in the art.

SUMMARY OF THE INVENTION

In accordance with the present invention, apparatus and methods for measuring cardiac output using a modified Fick Equation are provided where the amount of deadspace which is provided in the apparatus can be adjusted to increase or decrease the volume of exhalate to be re-breathed by the patient, thereby decreasing ventilation without changing airway pressure. The apparatus and methods of the present invention also provide an adjustability factor which enables the apparatus to be adjusted to suit any size or capacity of patient. The apparatus of the present invention also employs significantly less expensive elements of constriction thereby rendering the device disposable.

The apparatus and methods of the present invention apply a modified Fick Equation to calculate changes in p$CO_2$ flow and concentration to evaluate cardiac output. The traditional Fick Equation, written for $CO_2$ is:

$$Q = \frac{V_{CO_2}}{\left(C_{vCO_2} - C_{aCO_2}\right)}$$

where Q is cardiac output (when calculated using re-breathing techniques referred to as pulmonary capillary blood flow or "PCBF"), $V_{CO_2}$ is the output of $CO_2$ from the lungs and $$C_{a_{CO_2}} \text{ and } C_{v_{CO_2}}$$

are the arterial and venous $CO_2$ concentrations, respectively. It has been shown in prior work of others that cardiac output can be estimated from calculating the change in $pCO_2$, as estimated by end-tidal $C_2$ ("etCO$_2$"), as a result of a sudden change in ventilation. That can be done by applying a differential form of the Fick Equation as follows:

$$Q = \frac{V_{CO_{2_1}}}{(C_{v_1} - C_{a_1})} = \frac{V_{CO_{2_2}}}{(C_{v_2} - C_{a_2})}$$

where $C_a$ is arterial $CO_2$ concentration, $C_v$ is venous $CO_2$ concentration, and the subscripts 1 and 2 reference measured values before a change in ventilation and measured values during a change in ventilation, respectively. The differential form of the Fick Equation can, therefore, be rewritten as:

$$Q = \frac{V_{CO_{2_1}} - V_{CO_{2_2}}}{(C_{v_1} - C_{a_1}) - (C_{v_2} - C_{a_2})}$$

$$Q = \frac{\Delta V_{CO_2}}{\Delta C_{a_{CO_2}}} = \frac{\Delta V_{CO_2}}{s \Delta etCO_2}$$

where $\Delta_{VCO_2}$ is the change in $CO_2$ production in response to the change in ventilation, $$\Delta C_{a_{CO_2}}$$

is the change in arterial $CO_2$ concentration in response to the change in ventilation, $\Delta etCO_2$ is the change in end-tidal $CO_2$ concentration and s is the slope of the $CO_2$ dissociation curve. The foregoing differential equation assumes that there is no appreciable change in venous $CO_2$ concentration during the re-breathing episode, as demonstrated by Capek, et al., in their previous work. Also, a dissociation curve, well-known in the art, is used for determining $CO_2$ concentration based on partial pressure measurements.

In previous partial re-breathing methods, a deadspace, usually comprising an additional 50–250 ml capacity of air passage, was provided in the ventilation circuit to decrease the effective alveolar ventilation. In the present invention, a ventilation apparatus is provided with an adjustable deadspace to provide the necessary change in ventilation for determining accurate changes in $CO_2$ production and end-tidal $CO_2$ commensurate with the requirements of differently sized patients. In one embodiment of the ventilation apparatus, selectively adjustable deadspace is provided through which the patient exhales and inhales. Thus, the adjustable deadspace of the apparatus permits easy adjustment of the deadspace to accommodate any size or capacity of patient, from a small to a large adult. As a result, the patient is provided with a volume of re-breathable gas commensurate with the patient's size which decreases effective ventilation without changing the airway pressure. Because airway and intra-thoracic pressure are not affected by the re-breathing method of the present invention, cardiac output is not significantly affected by re-breathing. In an alternative method, the deadspace may be effectively lessened by selectively leaking exhaled gas from the ventilation system to atmosphere or to a closed receptacle means during inspiration.

The ventilation apparatus of the present invention includes a tubular portion which is placed in contact with the patient, and an inhalation conduit and exhalation conduit. In a common configuration, the inhalation conduit and exhalation conduit may be interconnected between a ventilator unit and the patient. Alternatively, however, a ventilator unit (i.e., a source of deliverable gas mechanically operated to assist the patient in breathing) need not be used with the ventilation apparatus and inhaled and exhaled breath is merely taken from or vented to atmosphere. Other conventional equipment commonly used with ventilator units or used in ventilation of a patient may be used with the inventive ventilation apparatus, such as a breathing mask.

An electrical pneurnotachometer for measuring flow of gas and a capnograph for measuring $CO_2$ concentrations are provided in proximity to the tubular portion between the inhalation and exhalation portions of the ventilation apparatus and the patient's lungs. The pneumotachometer and capnograph serve as detection apparatus for detecting changes in gas concentrations and flow and are in electrical communication with a computer having software designed to store and evaluate the measurements taken by the detection apparatus in real time. Other forms of detection apparatus may be used. Adjustable deadspace means are provided in connection with the exhalation portion of the ventilation apparatus, and may interconnect with the inhalation portion of the ventilation apparatus. In one embodiment, the adjustable deadspace means may be manually adjusted. Alternatively, electromechanical means may be interconnected between the computer and the adjustable deadspace means to provide automatic adjustment of the deadspace volume responsive to the size or capacity of the patient and responsive to changes in ventilation.

In an alternative embodiment, a tracheal gas insufflation apparatus is used to provide the change in ventilation necessary to calculate pulmonary $CO_2$ changes using the differential Fick Equation. Tracheal gas insufflation ("TGI") apparatus is commonly used to flush the deadspace of the alveolar spaces of the lungs and to replace the deadspace with fresh gas infused through insufflation means. That is, fresh gas is introduced to the central airway to improve alveolar ventilation and/or to minimize ventilatory pressure requirements. TGI apparatus is interconnected to a ventilator system and includes a means of introducing fresh gas into the breathing tube as it enters the patient's lungs. The TGI apparatus may be used in the methods of the present invention to determine baseline measurements of $VCO_2$ and $etCO_2$ during TGI. When the TGI system is turned off, a deadspace is formed by the patient's trachea and the endotracheal tube of the TGI apparatus which allows measurement of a change in $CO_2$ to be evaluated in accordance with the invention. Further, the catheter of the TGI apparatus may be variably positioned within the trachea of the patient to further adjust the deadspace volume.

The deadspace provided in the apparatus of the present invention causes a rapid drop in $VCO_2$ which thereafter increases slightly and slowly as the functional residual lung gas capacity equilibrates with the increase in alveolar $CO_2$ level. The change in $etCO_2$ rises more slowly after the addition of deadspace, depending on alveolar deadspace and cardiac output, but then stabilizes to a new level. A "standard," or baseline, breathing episode is conducted for a selected period of time immediately preceding the introduction of a deadspace (i.e., re-breathing) and $VCO_2$ and $etCO_2$ values are determined based on measurements made during the "standard" breathing event. Those values are substituted as the values $VCO_{2_1}$ and $C_{a_{CO2_1}}$ in the differential Fick Equation. $VCO_2$ and $etCO_2$ values are also determined from measurements taken approximately thirty seconds following the introduction of a deadspace during partial rebreathing to provide the second values (subscript 2 values) in the differential Fick Equation. The period of time during which partial re-breathing occurs and during which normal breathing occurs may be determined by the individual size and lung capacity of the patient. Additionally, the period of time between a re-breathing episode and a subsequent normal breathing episode may vary between patients depending on a particular patient's size and breath capacity. Thus, a thirty second time period for a breathing episode is only an average time and may be greater or lesser.

Cardiac output is determined, in the present invention, by estimating alveolar $CO_2$ concentration rather than basing output on end-tidal $CO_2$ concentration, as is practiced in the prior art. Partial pressure values that are obtained from $CO_2$ measurements are converted to a value for gas content in the blood using the dissociation equation known in the art. Thus, a more accurate cardiac output can be determined. In addition, the accuracy of cardiac output is increased by correcting $VCO_2$ values to account for flow of $CO_2$ into the functional residual capacity of the lungs, defined as the volume of gas left in the lungs at the end of an expired breath. The determination of values based on experiential data is processed by the software program to determine cardiac output.

The ventilation apparatus of the present invention employs inexpensive yet accurate monitoring systems as compared to the systems currently used in the art. The methods of the invention allow automatic adjustability of the apparatus for accommodating patients of different sizes and provides consistent monitoring with modest recovery time. Further, the present apparatus and methods can be used equally with non-responsive, intubated patients as well as non-intubated, responsive patients.

BRIEF DESCRIPTION OF THE DRAWINGS

In the drawings, which illustrate what is currently considered to be the best mode for carrying out the invention.

DETAILED DESCRIPTION OF THE ILLUSTRATIONS

Figure 1:
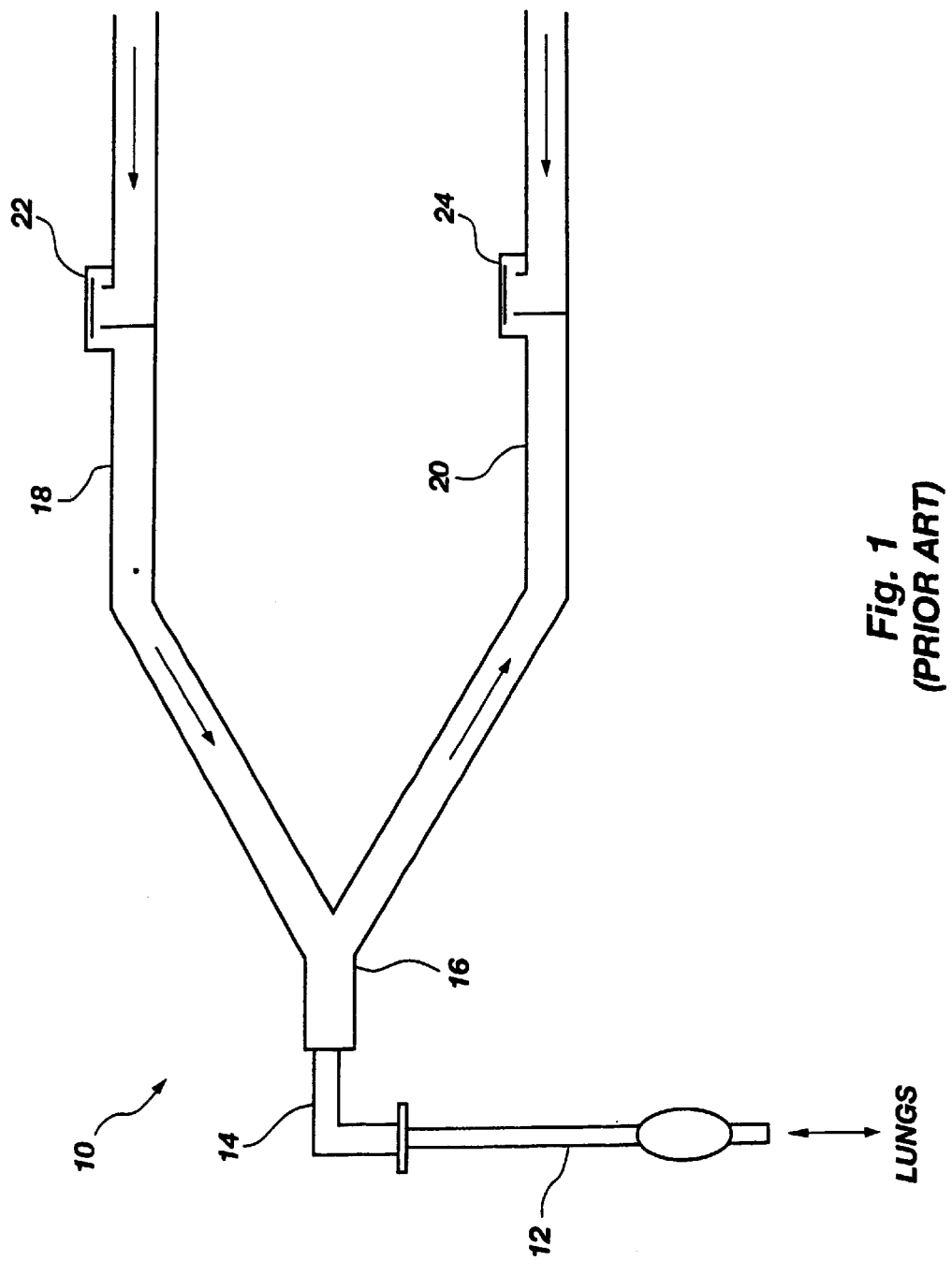
FIG. 1 is a schematic representation of conventional ventilation systems used for assisting patient breathing.

For comparative purposes, FIG. 1 schematically illustrates a conventional ventilation system which is typically used with patients who require assisted breathing during an illness, a surgical procedure or recovery from a surgical procedure. The conventional ventilator system 10 includes a tubular portion 12 which is inserted into the trachea by intubation procedures. The distal end 14 of the tubular portion 12 is fitted with a Y-piece 16 which interconnects an inspiratory hose 18 and an expiratory hose 20. Both the inspiratory hose 18 and expiratory hose 20 are connected to a ventilator machine (not shown) which delivers air to the inspiratory hose 18. A one-way valve 22 is positioned on the inspiratory hose 18 to prevent exhaled gas from entering the inspiratory hose 18 beyond the valve 22. A similar one-way valve 24 on the expiratory hose 20 limits movement of inspiratory gas into the expiratory hose 20. Exhaled air flows passively into the expiratory hose 20.

Figure 2:
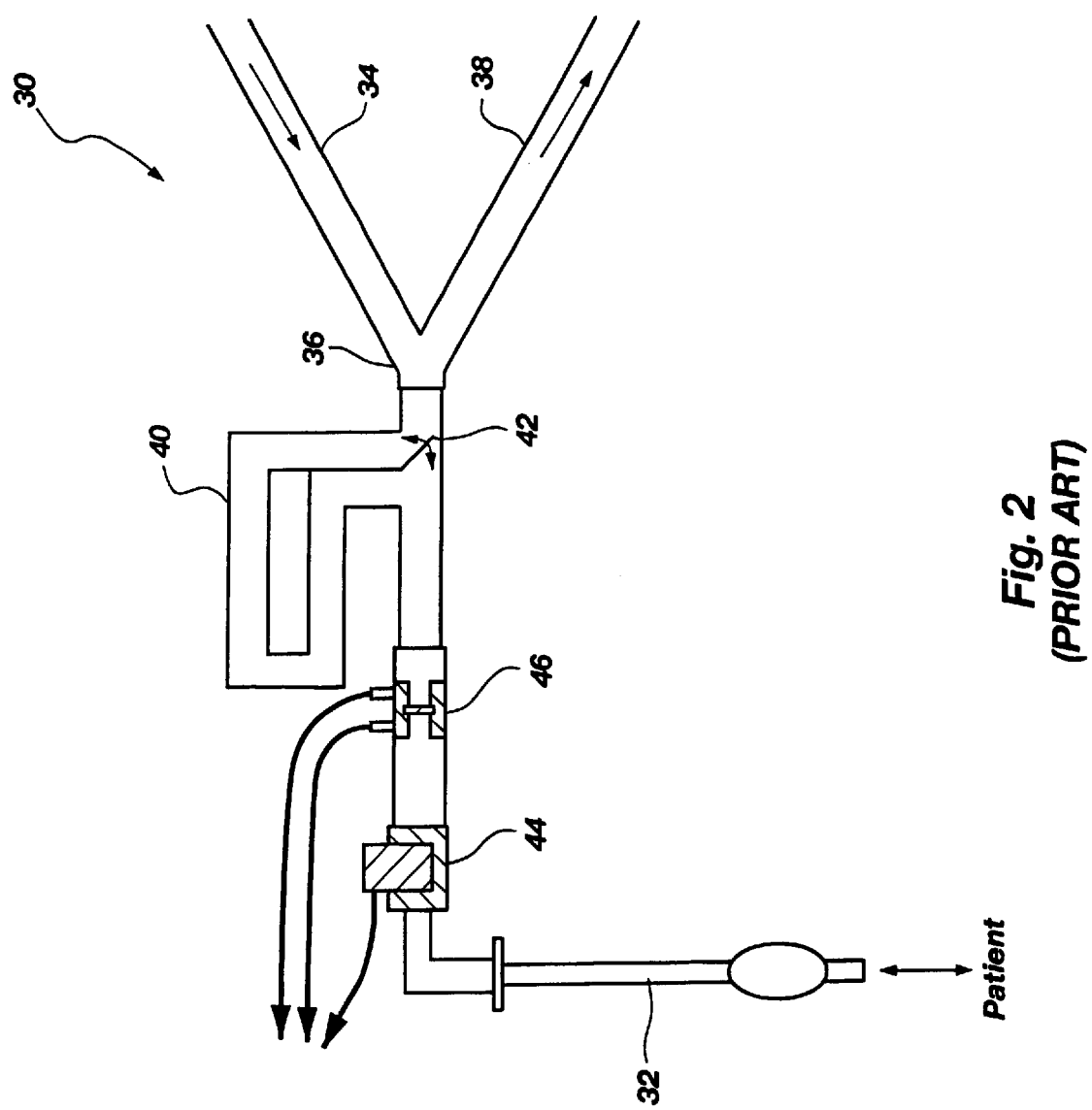
FIG. 2 is a schematic representation of prior art re-breathing systems.

In known re-breathing ventilation circuits 30, as shown in FIG. 2, the tubular portion 32 is inserted into the trachea of the patient by intubation procedures, and gas is provided to the patient from a ventilator machine (not shown) via an inspiratory hose 34 which is interconnected by a Y-piece 36 to an expiratory hose 38. An additional length of hose 40 is provided between the tubular portion 32 and the Y-piece 36 which acts as a deadspace for receiving exhaled gas. A three-way valve 42 generally positioned between the Y-piece 36 and the opening to the additional length of hose 40 is constructed for intermittent actuation to selectively direct the flow of gas. That is, at one setting, the valve 42 allows inspiratory gas to enter the tubular portion 32 while preventing movement of the gas into the additional length of hose 40. In a second setting, the valve 42 allow exhaled gas to enter into the expiratory hose 38 while preventing movement of gas into the additional length of hose 40. In a third setting, the three-way valve 42 directs exhaled air to enter into the additional length of hose 40 and causes the patient to re-breath the exhaled air on the following breath to thereby cause a change in effective ventilation.

The change in $VCO_2$ and end-tidal $CO_2$ caused by the change in ventilation in the prior art system of FIG. 2 can then be used to calculate cardiac output. Sensing and/or monitoring devices may be attached to the re-breathing ventilation circuit 30 between the additional length of hose 40 and the tubular portion 32, The sensing and/or monitoring devices may include, for example, means 44 for detecting $CO_2$ concentration and means 46 for detecting flow parameters during inhalation and exhalation. Those sensing and/or monitoring devices are typically connected to data recording and display equipment (not shown). One problem encountered in use of the prior art system is that the deadspace provided by the additional length of hose 40 is fixed and may not be adjusted. As a result, the amount of deadspace provided in the circuit for a small adult to effect re-breathing is the same amount of deadspace available for a large adult to effect re-breathing, and the resulting changes in $CO_2$ values for patients of different sizes derived from fixed-deadspace systems, can produce inadequate evaluation of cardiac output. Further, the three-way valve 40 of the system is expensive and significantly increases the cost of the ventilation device.

Figure 3:
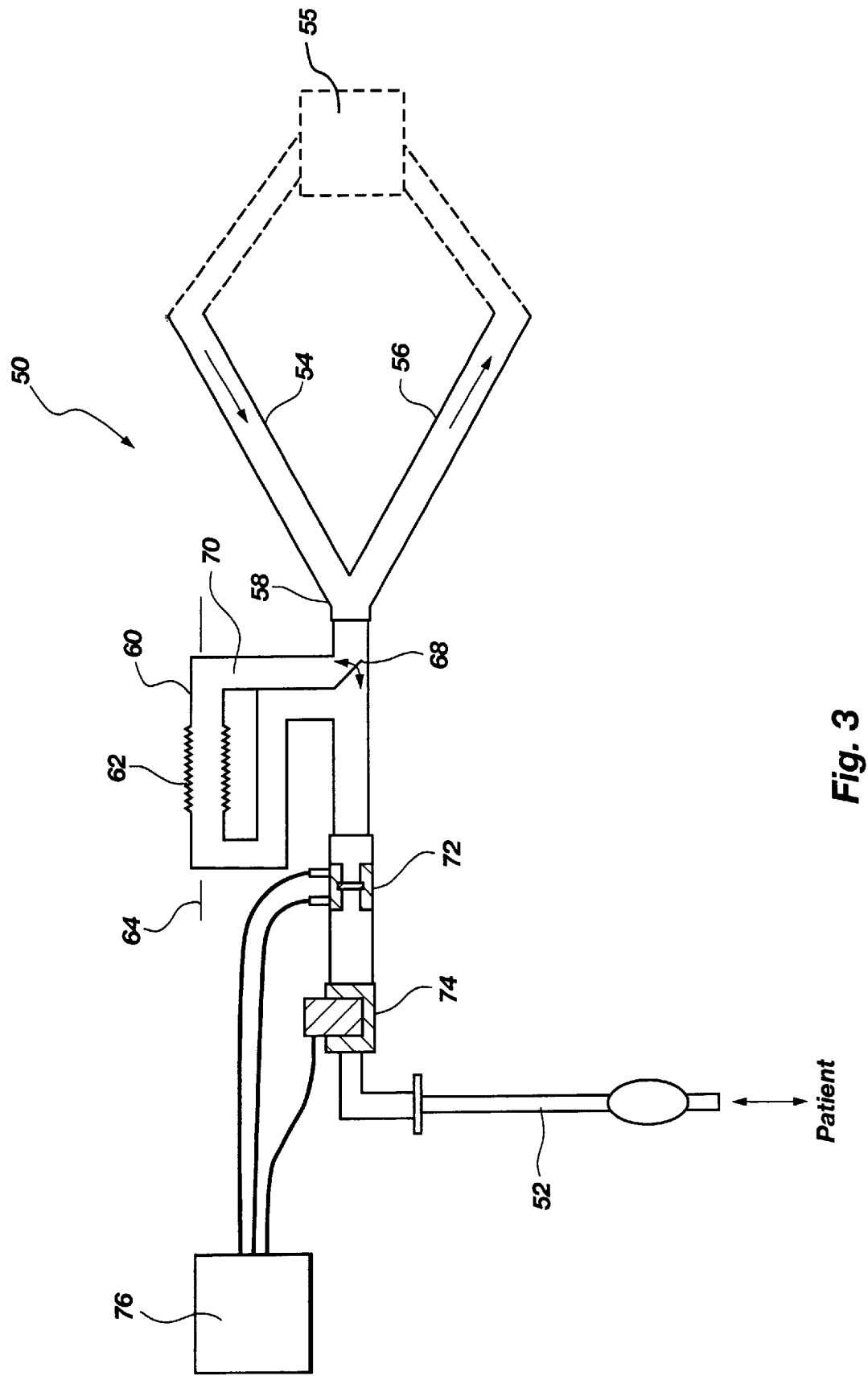
FIG. 3 is a schematic first embodiment of the ventilation apparatus of the present invention illustrating an adjustably expandable deadspace.

FIG. 3 illustrates the ventilation apparatus of the present invention which provides an improvement over known ventilation devices used to detect or monitor cardiac output. The present ventilation apparatus 50 comprises a tubular airway 52 which is placed in communication with the patient's lungs. Although the present ventilation apparatus 50 may be placed in communication with the trachea by intubation procedures as is done in the prior art, the present ventilation apparatus 50 need not be inserted directly into the trachea of the patient. Alternatively, a breathing mask may be used for positioning over the patient's nose and mouth. Thus, the present invention may be used with unconscious or uncooperative patients needing ventilation assistance and may be used with equal efficacy with patients who are conscious. The ventilation apparatus 50 also includes an inspiratory hose 54 and an expiratory hose 56 which may be each ventilated to atmosphere or may be connected to a ventilator machine 55 (shown in phantom) which provides gas for delivery to the patient through the inspiratory hose 54. The inspiratory hose 54 and expiratory hose 56 may be joined together by a Y-piece 58.

The Y-piece 58 connects to an additional length of conduit or hose 60 which provides a deadspace for receiving exhaled gas from the patient. However, the additional length of hose 60 is structured to be selectively expandable to readily enable the volume of deadspace to be adjusted commensurate with the size or lung capacity of the patient, or to other ventilation parameters, such as increased or decreased tidal volume or modified respiration rate. As suggested by the schematic drawing of FIG. 3, selective expansion of the deadspace may be accomplished by structuring the additional length of hose 60 with an expandable section 62 made of, for example, a piece of corrugated hose which can be lengthened or shortened by simply pulling or pushing the expandable section 62 along its longitudinal axis 64. The corrugated hose will retain the length at which it is positioned until adjusted again. Other suitable means of providing adjustable expansion of the volume of the deadspace are available, extending the length of the hose 60 being but one approach. A three-way valve 68 may be connected to the additional length of hose 60 to force inspiratory gas to enter the deadspace 70 upon inhalation. The three-way valve 68 is also structured to selectively prevent exhaled gas from entering the deadspace 70 during normal breathing or to direct exhaled gas into deadspace 70 during re-breathing episodes so that the patient is forced to re-breath exhaled gas from the deadspace 70.

A flow meter 72, or pneumotachometer, is attached to the ventilation apparatus 50 at a point between the tubular airway 52 and the additional length of hose 60. The flow meter 72 detects gas flow through the ventilation apparatus 50. A $CO_2$ sensor 74, or capnograph, is also connected to the ventilation apparatus 50 between the tubular airway 52 and the additional length of hose 60. The $CO_2$ sensor 74 detects changes in $CO_2$ resulting from a change in ventilation, the data from which is used to calculate cardiac output. The $CO_2$ sensor 74 may be an "on airway" sensor, a sampling sensor of the type which withdraws a side stream sample of gas for testing, or any other suitable $CO_2$ sensor. Both the flow meter 72 and $CO_2$ sensor 74 are connected to a computer 76 which is programmed to store and analyze data from the flow meter 72 and $CO_2$ sensor 74, and to calculate from the data the estimated cardiac output of the patient As previously described herein, the differential Fick Equation requires a change in pulmonary gas concentration and output to be induced in the patient in order to estimate cardiac output. Re-breathing gas previously exhaled by the patient increases the amount of $CO_2$ breathed in by the patient and enables the evaluation of increased $CO_2$ levels during a change in effective ventilation as compared to standard $CO_2$ levels during normal ventilation. The ventilation apparatus of the present invention provides the ability to selectively adjust the deadspace required in re-breathing to increase the amount of gas ($CO_2$) re-breathed by the patient from the previous exhalation. The ventilation apparatus of the present invention also allows the ventilation circuit to be adjusted automatically in accordance with the size or capacity of a patient, and in response to ventilation parameters. That is, if the detected change in $etCO_2$ is less than 3 mm Hg, or the change in $VCO_2$ is less than 0.2 times the $VCO_2$, then the deadspace volume should be increased by twenty percent.

Figure 4:
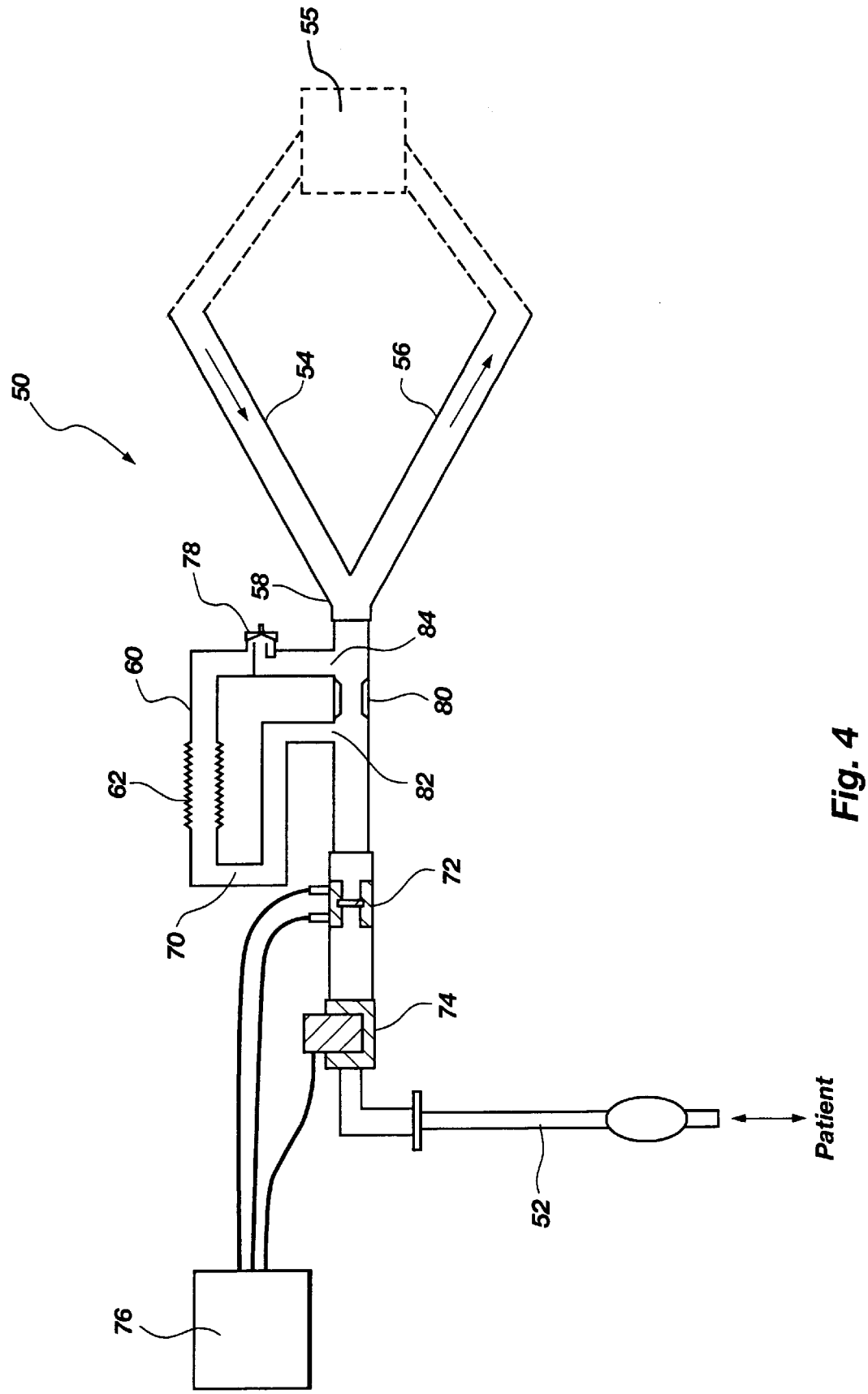
FIG. 4 is a schematic representation of an alternative embodiment of the present invention where the re-breathing circuit is constructed with a leak valve.

In an alternative embodiment of the apparatus 50 of the invention, as shown in FIG. 4, the expense of using a three-way valve may be eliminated by structuring the additional length of hose 60 with an inexpensive two-way valve 78 and by positioning a flow restrictor 80 between the inlet 82 and outlet 84 of the deadspace 70. Thus, when the two-way valve 78 is closed, gas to and from the ventilator machine will be directed through the flow restrictor 80 and to the patient. During a re-breathing episode, the two-way valve 78 is open so that the exhaled air, encountering the flow restrictor 80, follows the course of less resistance through the deadspace 70. Thus, the deadspace 70 may be adjusted at the expandable section 62 to provide the necessary deadspace 70 for calculating changes in cardiac output.

Figure 5:
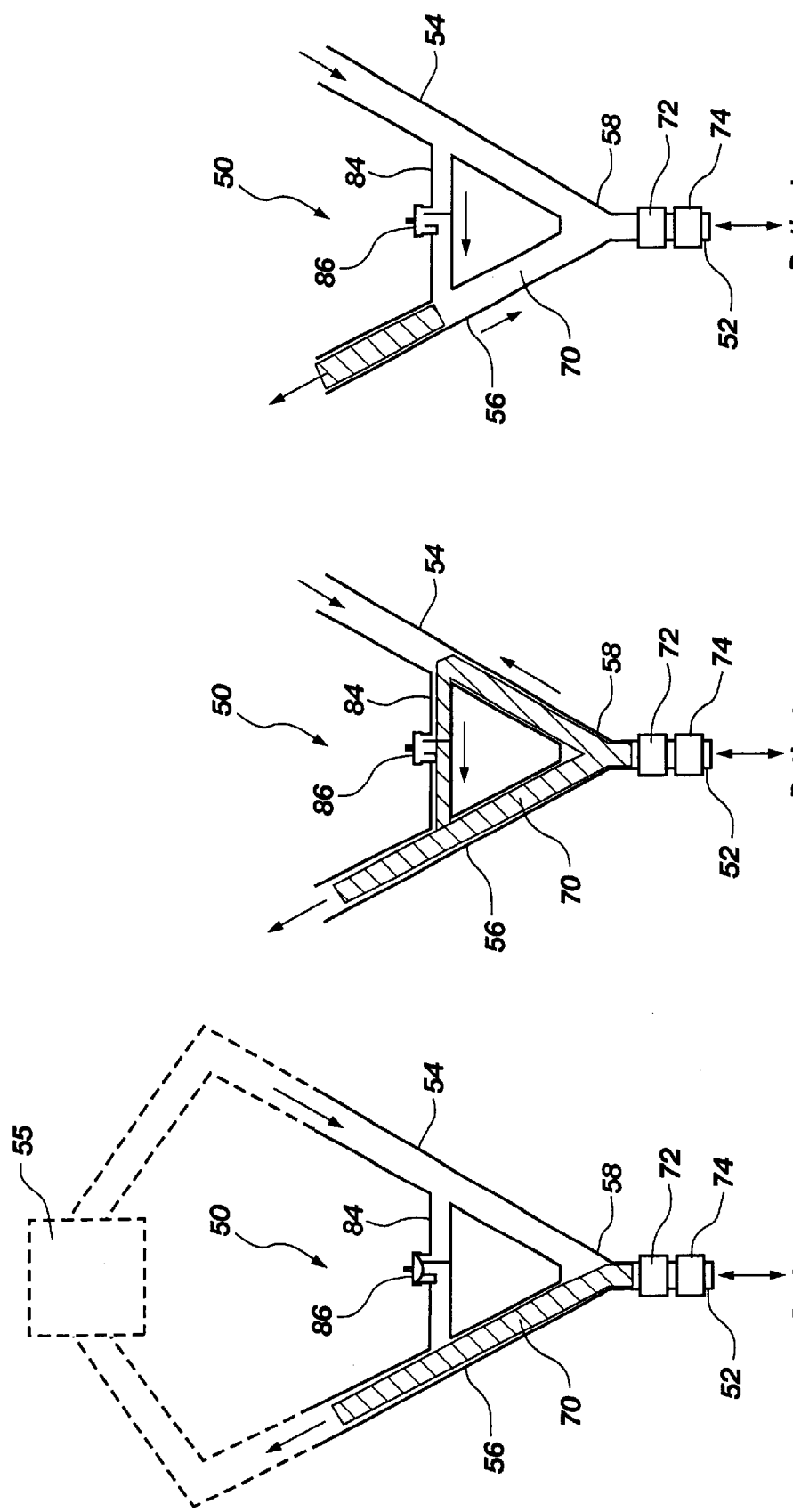
FIGS. 5(A)–(C) are a schematic representation of another alternative embodiment of the present invention where the inhalation portion and exhalation portion of the ventilation circuit are interconnected and have a two-way closeable valve.

In another alternative embodiment of the ventilation apparatus 50 of the present invention, as shown in FIGS. 5(A)–(C), a shunt line 84 is positioned between the inspiratory hose 54 and the expiratory hose 56 to provide selectively sized deadspace 70 in the circuit. The structure of the embodiment shown in FIGS. 5(A)–(C) causes the inspiratory hose 54 and expiratory hose 56 to act as part of the deadspace 70, as well. A two-way shunt valve 86 positioned on the shunt line 84 selectively directs the flow of inspired and expired gas dependent upon whether the shunt valve 86 is open or closed. Thus, when the ventilation apparatus 50 is configured for normal or baseline breathing, as depicted in FIG. 5(A), exhaled air (represented by the shaded area) will enter the expiratory hose 56. During normal breathing, the shunt valve 86 is closed. When the ventilation apparatus 50 is configured for a re-breathing episode, as depicted in FIG. 5(B), the shunt valve 86 is opened and exhaled gas may fill a portion of the inspiratory hose 54, all of the expiratory hose 56 and the shunt line 84, all of which serve as the deadspace 70.

Figure 6:
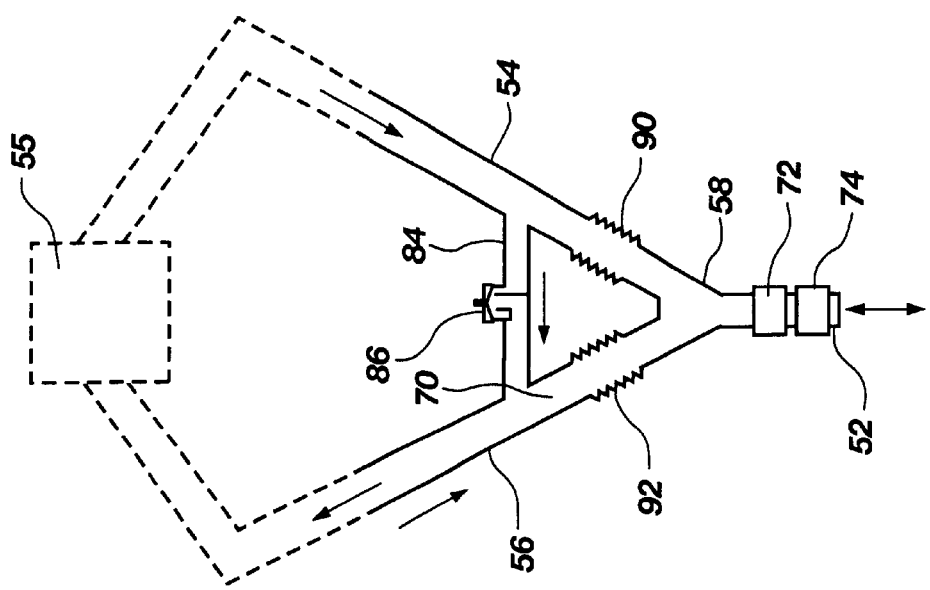
FIG. 6 is a schematic representation of an alternative embodiment similar to the embodiment shown in FIG. 5, but where the inhalation and exhalation portions are adjustably expandable.

The deadspace 70 in the embodiment shown in FIGS. 5(A)–(C) may be rendered adjustably expandable, as shown in FIG. 6, by structuring the inspiratory hose 54 with an expandable section 90 positioned between the shunt line 84 and the Y-piece 58, and by structuring the expiratory hose 56 with an expandable section 92 positioned between the shunt line 84 and the Y-piece 58. Thus, the deadspace 70 can be selectively adjusted in accordance with the size or capacity of the patient, or responsive to operating conditions, by increasing that portion of the inspiratory hose 54 and expiratory hose 56 extending from the Y-piece 58. Any suitable adjustably expandable means may be used. As suggested by FIG. 6, however, the expandable section 90, 92 may be made from corrugated plastic material, the length of which can be easily expanded or contracted, and the plastic material will maintain its adjusted length until repositioned. The embodiment of FIG. 6 provides a particularly simple and inexpensive construction rendering a particularly preferred embodiment because of its ease of use and disposability.

Figure 7:
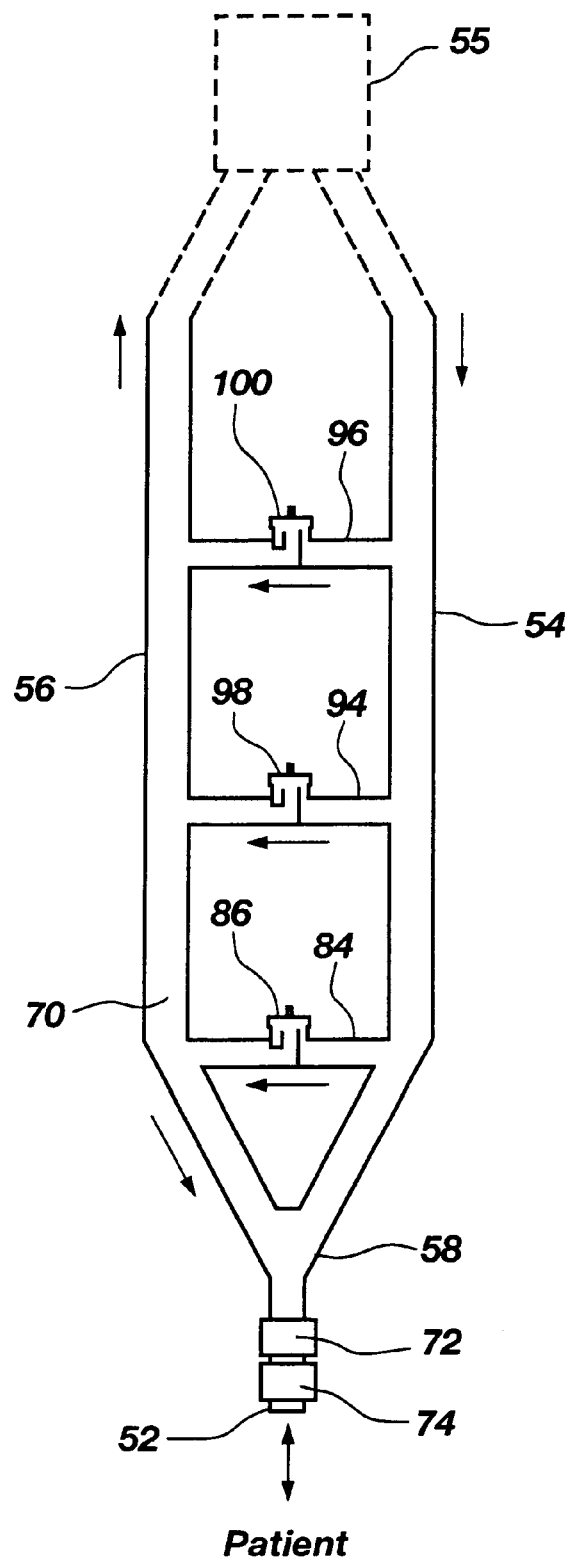
FIG. 7 is a schematic representation of another embodiment of the invention where a series of valves is provided along the length of the inhalation and exhalation portions to provide a selectable volume of deadspace dependent upon the size and/or capacity of the patient.
Figure 12:
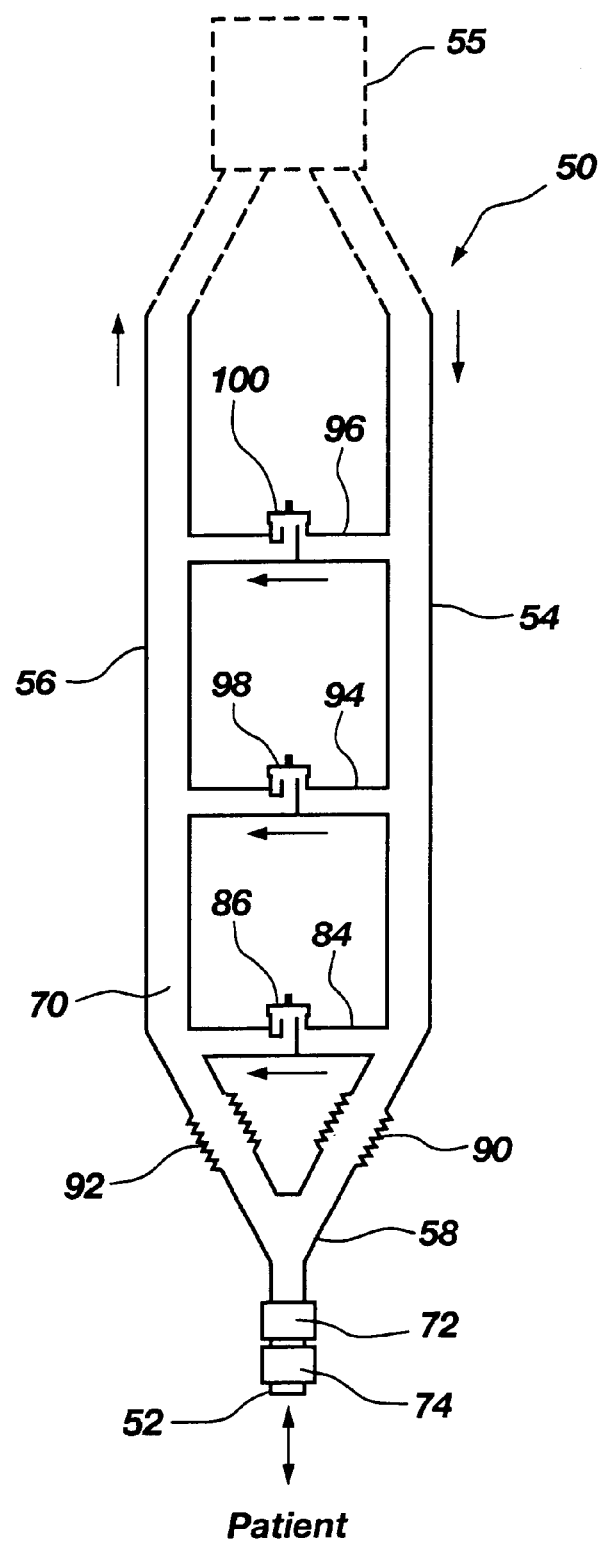
FIG. 12 is a schematic representation of an alternative embodiment of the invention shown in FIG. 7 which includes variably expandable inhalation and exhalation portions.

In yet another embodiment of the ventilation apparatus 50 of the present invention, as shown in FIG. 7, the amount of available deadspace 70 may be selectively adjusted by providing a plurality of shunt lines 84, 94, 96 positioned between the inspiratory hose 54 and the expiratory hose 56, with each shunt line 84, 94, 96 being structured with a two-way shunt valve 86, 98, 100. In operation, the amount of deadspace 70 required, as dictated by the size or capacity of the patient, may be selectively provided by using any suitable number of shunt lines 84, 94, 96 to allow exhaled gas to move through the ventilation apparatus 50. For example, given a patient of average size or lung capacity, it may be appropriate to use the first shunt line 84 and the second shunt line 94 as potential deadspace 70. Thus, as the patient exhales in a re-breathing episode the shunt valves 86, 98 associated with the first shunt line 84 and second shunt line 94 may be opened, allowing exhaled and re-breathable gas to fill the expiratory hose 56, the inspiratory hose 54 between the second shunt line 94 and the Y-piece 58, the first shunt line 84 and the second shunt line 94. With a patient of larger size or greater lung capacity, it may be necessary to use the third shunt line 96 as well in providing sufficient deadspace 70 for re-breathing. Notably, each shunt valve 86, 98, 100 may be in electromechanical communication with the computer 76 (not shown in FIG. 7) so that the computer may determine, from the pneumotachometer, for example, that additional deadspace 70 is required and cause the opening of one or more of the shunt valves 86, 98, 100 to provide sufficient additional deadspace 70. In an alternative embodiment, the ventilation apparatus 50 shown in FIG. 7 may be modified by the addition of selectively expandable sections 90, 92 as shown in FIG. 12.

Figure 8A:
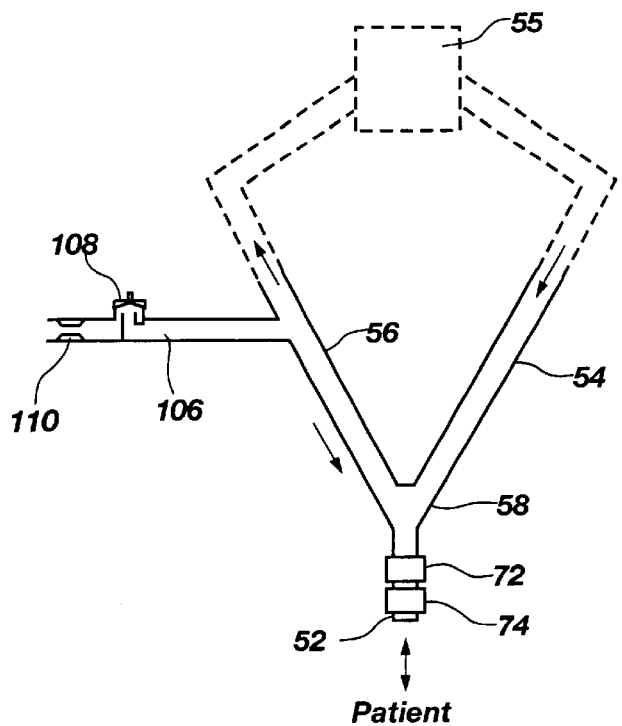
FIGS. 8(A) and (B) are schematic representations of another embodiment of the invention where a leak valve is provided, both with a vent to atmosphere and to a parallel compliance chamber.

In the several alternative embodiments of the invention previously illustrated and described, the amount or volume of the deadspace has been selectively adjustable by providing means for adjusting the volume of the deadspace, such as by providing length expanding means. It may be equally appropriate, however, to provide a change in ventilation, as required by the differential Fick Equation, by leaking some of the exhaled gas out of the system during the inspiration phase of a breath. Thus, as illustrated by FIG. 8(A), the ventilation apparatus 50 of the present invention may be structured with an evacuation line 106 connected to the expiratory hose 56 of the ventilation apparatus 50. The evacuation line 106 may be structured with gas releasing structure, such as a simple valve 108 connected thereto which, when opened, allows exhaled gas to move through the evacuation line 106. An orifice 110 positioned at the end of the evacuation line 106 allows some of the exhaled gas to escape to the atmosphere.

Figure 8B:
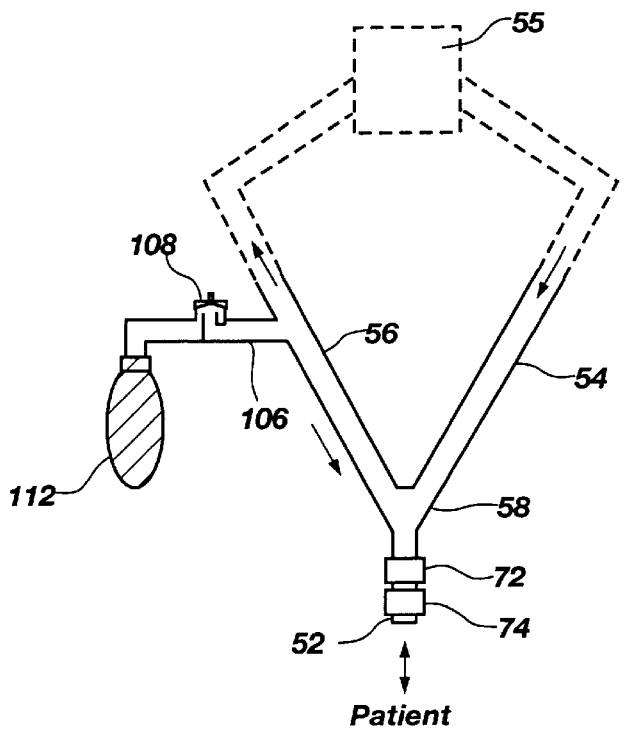

When and how much exhaled gas should be leaked from the ventilation apparatus 50 during a re-breathing event may be determined by the computer (not shown in FIG. 8) in response to flow conditions, $CO_2$ conditions and/or the size or lung capacity of the patient. The valve 108, in electromechanical communication with the computer, may be selectively actuated according to ventilation or patient conditions. Where a patient is anesthetized or is otherwise exhaling gas which is undesirable for venting to the atmosphere, a compliant chamber 112, such as an expandable bag shown in FIG. 8(B), may be attached to the evacuation line 106 to receive the exhaled gas leaked from the ventilation circuit.

Figure 9:
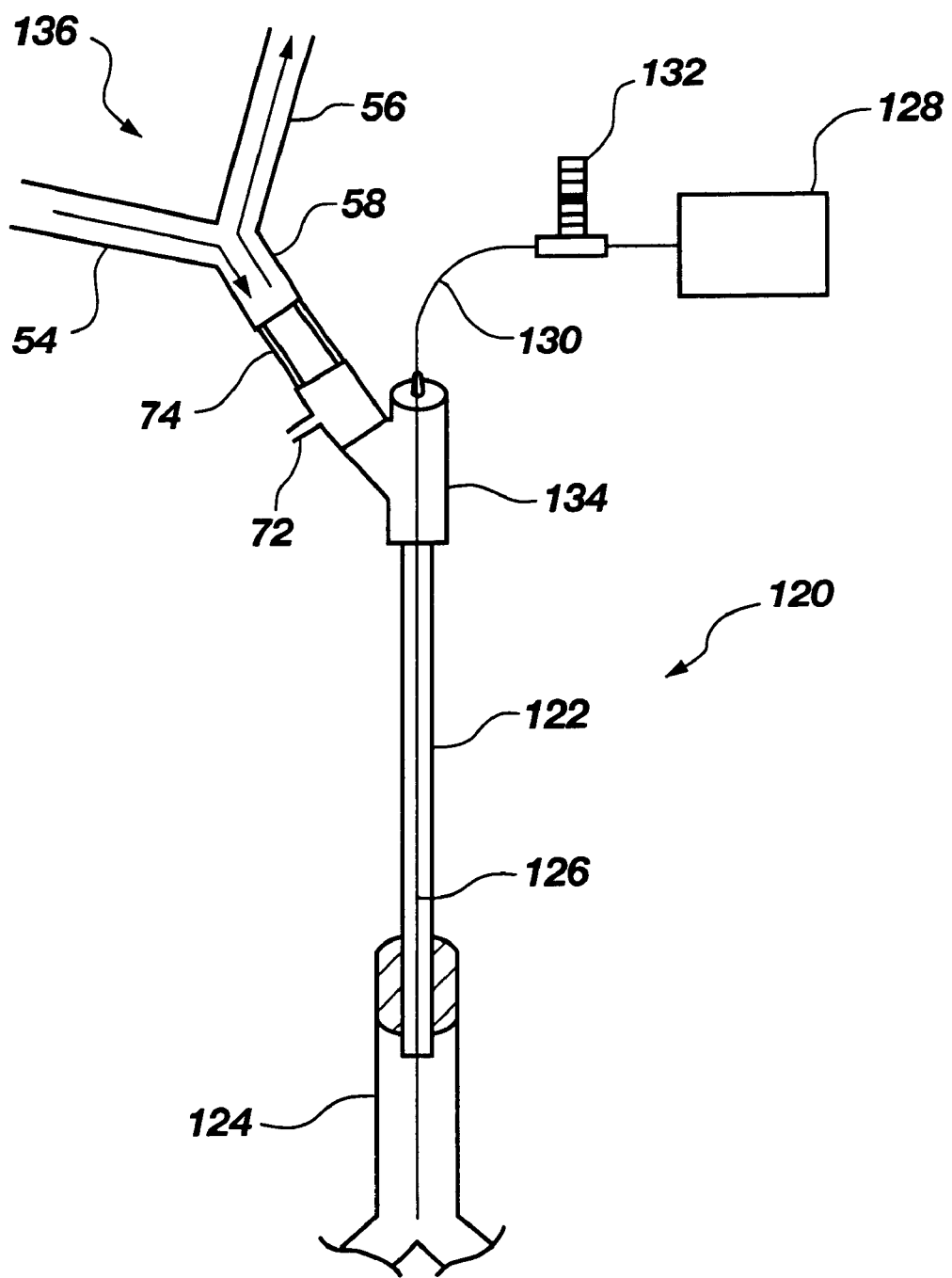
FIG. 9 is a schematic representation of a tracheal gas insufflation apparatus of the present invention which can be used to provide a necessary change in ventilation with a deadspace.

FIG. 9 schematically illustrates the use of a tracheal gas insufflation (TGI) apparatus 120 to provide the necessary deadspace in determining cardiac output in patients. TGI apparatus is typically used to ventilate sick patients who require the injection of fresh gas into their central airway for the improvement of alveolar ventilation. TGI apparatus can be configured to provide continuous or phasic (e.g., only during inhalation) injections of gas, The TGI apparatus supplies gas, or an oxygen/gas mixture, to the lungs with every breath. As shown in FIG. 9, the TGI apparatus comprises an endotracheal tube 122 which is inserted into the trachea 124 of the patient by intubation procedures. A catheter 126 extends through the endotracheal tube 122 and into the patient's lungs, typically just above the carina. Gas or an oxygen/gas blend is provided from a gas source 128 and is directed through gas tubing 130 into the catheter 126. A flow meter 132 may assist in determining the optimum amount of gas to be introduced into the lungs.

An adaptor fitting 134 may be used to connect a ventilation circuit 136 of a type previously described to the TGI apparatus 120. That is, a ventilation circuit 136 comprising a Y-piece 58 from which extends an inspiratory hose 54 and an expiratory hose 56 is structured with a flow meter line 72 attachable to a flow meter (not shown) and a $CO_2$ sensor 74 for collecting data derived during a re-breathing event. In the illustrated TGI apparatus 120, the endotracheal tube 122 provides deadspace 70 required for re-breathing in addition to the ventilation circuit 136 as previously described. To act as a deadspace, however, the TGI apparatus (i.e., the gas source 128 and flow meter 132 ) must be turned off, reduced or otherwise disabled. Exhaled air is thereby allowed to fill the endotracheal tube 122 and enter through the Y-piece 58. The endotracheal tube 122 and ventilation circuit 136 serve as deadspace when the TGI apparatus 120 is turned off. The volume of deadspace provided by the TGI apparatus configuration may be further increased or decreased as necessary, by varying the depth to which the catheter 126 is positioned in the patient's trachea.

The computer to which the flow meter 72 and $CO_2$ sensor 74 are connected is programmed to receive data collected by the flow meter 72 and $CO_2$ sensor 74 and to analyze the data to calculate an estimated cardiac output. The parameters which are required by the software program to analyze the data and to estimate cardiac output are described hereafter.

The calculation of cardiac output for a given patient is based on the collection of data from the $CO_2$ sensor and flow meter attached to the ventilation apparatus of the present invention. Raw flow and $CO_2$ signals from the flow meter and $CO_2$ sensor 74 are filtered to remove artifacts and the flow signals, $CO_2$ signals and pressure signals are stored in a buffer in the software program. When the flow signal crosses a prescribed threshold (e.g., 15 liters/minute), the buffer is searched to find the most recent zero-crossing. The zero-crossing is identified as the start of a new breath. All data stored in the buffer since the last zero-crossing and the crossing of the prescribed threshold (i.e., the new zero-crossing) is established as one breathing cycle. For each breathing cycle, the parameters of the breathing phase are calculated as follows:

1) $etCO_2$: The average concentration of $CO_2$ during the final 5% of expiratory tidal volume is taken as end-tidal $CO_2$.
2) $VCO_2$: The integral of flow (in milliliters) multiplied by concentration of $CO_2$ over the entire breath is $VCO_2$.
3) Inspired $CO_2$: This is the concentration of inspired $CO_2$. It is the integral of $CO_2$ concentration times the volume (in milliliters) of air flow during inspiration (i.e., negative flow).
4) Airway deadspace: Determined as the expired volume (in milliliters) at which $CO_2$ concentration crosses a selected threshold set at, for example, 0.5 times $etCO_2$.

The initial values of $VCO_2$ and $etCO_2$ are filtered employing a three-point median filter. The $etCO_2$ and $VCO_2$ signals are straight-line interpolated and re-sampled at 0.5 Hz.

A correction is made in the $VCO_2$ value to account for alveolar deadspace. That is, the correction in $VCO_2$ corrects for the flow of $CO_2$ into lung stores such as the functional residual capacity (FRC) in the lungs, or, in other words, the volume of gas left in the lungs at the end of a breath. Alveolar deadspace is demonstrated more clearly in FIG. 10, which schematically illustrates the lungs 150 of a patient. The lungs 150 generally comprise the trachea 152, bronchi 154 and alveoli 156. The trachea 152 and bronchi 154 generally comprise what is known as the anatomic or serial deadspace, which exists in the region indicated between arrows A and B. In the lungs 150, there are alveoli 156 which are perfused with blood (i.e., in contact with blood flow to provide oxygenation to the blood) and alveoli which are not perfused, though both perfused and un-perfused alveoli 156 may be ventilated.

Figure 10:
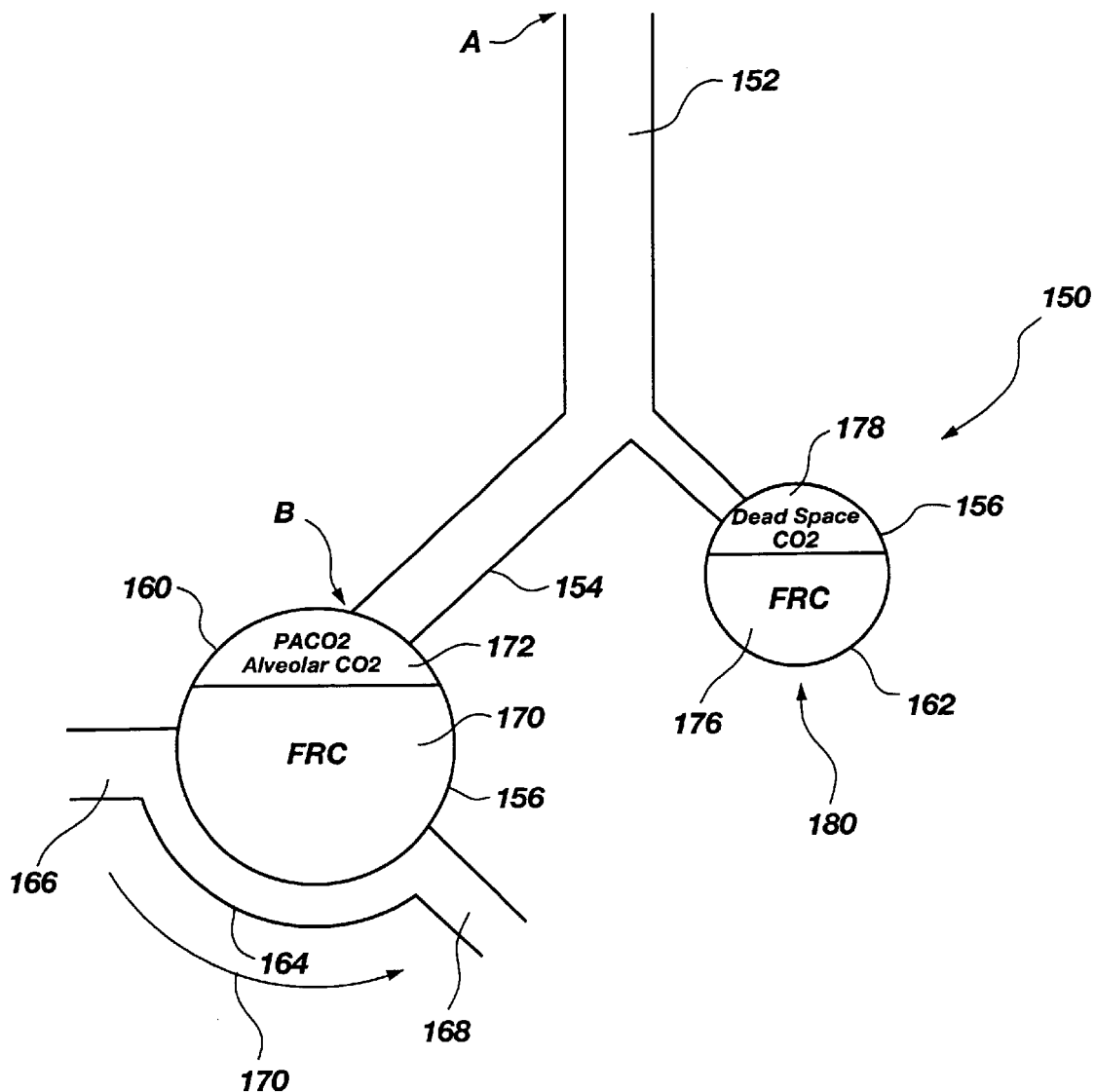
FIG. 10 is a schematic representation of human lungs illustrating the concepts of parallel deadspace, alveolar deadspace and serial deadspace in the lungs of a patient.

Perfused alveoli 160 and unperfused alveoli 162 are illustrated in FIG. 10. The perfused alveoli 160 are contacted with blood flowing through minute capillaries 164 surrounding the alveoli 160, the venous blood 166 flowing toward the alveoli 160 and the arterial blood 168 flowing away from the alveoli 160 in the direction of arrow 170. In the alveoli 160, 180, a volume of gas known as the functional residual capacity (FRC) 176 remains in the alveoli following exhalation. A portion 172 of the alveoli 160 which is evacuated upon exhalation (i.e., is ventilated) is representational of alveolar $CO_2$ ($PA_{CO_2}$). In un-perfused alveoli 162, the FRC 176 contains gas which is not evacuated during a breath, and the ventilated portion 178 of the alveoli 162 forms a space containing gas or $CO_2$ which is ventilated, but not perfused. It is the ventilated portion 178 existing in the un-perfused alveoli 162 which comprises parallel deadspace (PDS), so called because it is ventilated in parallel with the perfused alveoli.

In the present invention, the software program compensates, or accounts, for the functional residual capacity of the patient's lungs and the alveolar deadspace which exists. The correction is equal to the FRC times the change in end-tidal concentration or $$VCO_2 = VCO_2 + FRC \times \Delta etCO_2 / Pbar,$$

where "Pbar" is barometric pressure. FRC is estimated as a function of body weight as estimated by the deadspace volume using the equation $$FRC = FRC\text{-factor} \times \text{airway deadspace} + \text{an off-set value,}$$

where the FRC-factor is a value experimentally determined or is based on published data known in the art and the off-set value is a fixed constant which is added to compensate for breathing masks or other equipment components which may add deadspace to the circuit and thereby unacceptably skew the relationship between FRC and deadspace. The airway deadspace is the volume at which $CO_2$ crosses a selected threshold [e.g., $0.5etCO_2$]. Dry gas is assumed in all equations.

Compensation is also made for parallel deadspace (See FIG. 10). Parallel dead space $CO_2$ concentration is calculated as a low pass filtered version of the mixed inspired $CO_2$ plus the airway deadspace times the previous end-tidal $CO_2$ concentration. The average $CO_{2PDS}$ is $etCO_2$ times airway deadspace plus inspired $CO_2$ volume divided by the tidal volume. Breath-by-breath calculation of parallel deadspace, or unperfused space, concentration is therefore:

$$CO_{2PDS}(n) = [FRC/(FRC+V_t)] \times CO_{2PDS}(n-1) + ([Vi_{CO_2} + \text{deadspace} \times etCO_2(n-1)]/V_t) \times [V_t/(V_t + FRC)]$$

where $V_t$ is the tidal volume (the volume of the breath), PDS is parallel deadspace (i.e., space in the lung that is ventilated but not perfused by blood flow), $etCO_2$ is the concentration of $CO_2$ at the end of the exhaled breath, or "end-tidal," "deadspace" is the volume in the trachea and bronchi through which air must pass to get to the alveoli but in which no gas exchange occurs (also defined as "serial dead space," See FIG. 10) and (n−1) indicates the previous breath.

Alveolar $CO_2$ partial pressure ("$PA_{CO_2}$") is calculated from the end-tidal $CO_2$ and the $CO_2$ in the parallel deadspace. Thus, if $$etCO_2 = r \times PA_{CO_2} + (1-r)PDS_{CO_2},$$

then $$PA_{CO_2} = [etCO_2 - (1-r)PDS_{CO_2}]/r,$$

where r is the perfusion ratio calculated as the ratio of perfused alveolar ventilation divided by total alveolar ventilation, or $(V_A - V_{PDS})/V_A$. The perfusion ratio r is estimated to be about 0.92. Perfusion ratio can also be estimated by direct analysis of arterial blood.

The $PA_{CO_2}$ signal is then converted to $CO_2$ content using the following equation:

$$C_{CO_2} = (6.957 \times Hb + 94.864) \times ln(1 + 0.1933(P_{CO_2})),$$

where $C_{CO_2}$ is the concentration of $CO_2$ and Hb is hemoglobin concentration. In some instances, a hemoglobin count may be readily available and is used in the equation. If hemoglobin (Hb) concentration is not available the value of 11.0 is used in the software program.

Baseline values of $etCO_2$ and $VCO_2$, also referred to herein as "before $CO_2$ and before $VCO_2$," are those values which exist during normal breathing and are calculated as the average of all samples between 27 and 0 seconds before the start of re-breathing. Once a re-breathing episode begins, the $VCO_2$ value during re-breathing, also referred to herein as "during $VCO_2$," is calculated as the average $VCO_2$ between 25 and 30 seconds of re-breathing. The calculation of $C_{CO_2}$ during a re-breathing episode is determined using a regression line to predict the stable concentration of alveolar $CO_2$ ($C_{CO_2}$). To predict the $C_{CO_2}$ at which the signal will be stable (i.e., unchanging), the $C_{CO_2}$ is plotted versus the breath-to-breath change in concentration. The line is regressed and the intersection between the $C_{CO_2}$ and zero $\Delta C_{CO_2}$ is the predicted stable point.

Cardiac output is then calculated as follows:

$$CO_2 = [\text{before } V_{CO_2} - \text{during } V_{CO_2}] / [\text{during } C_{CO_2} - \text{before } C_{CO_2}].$$

Figure 11:
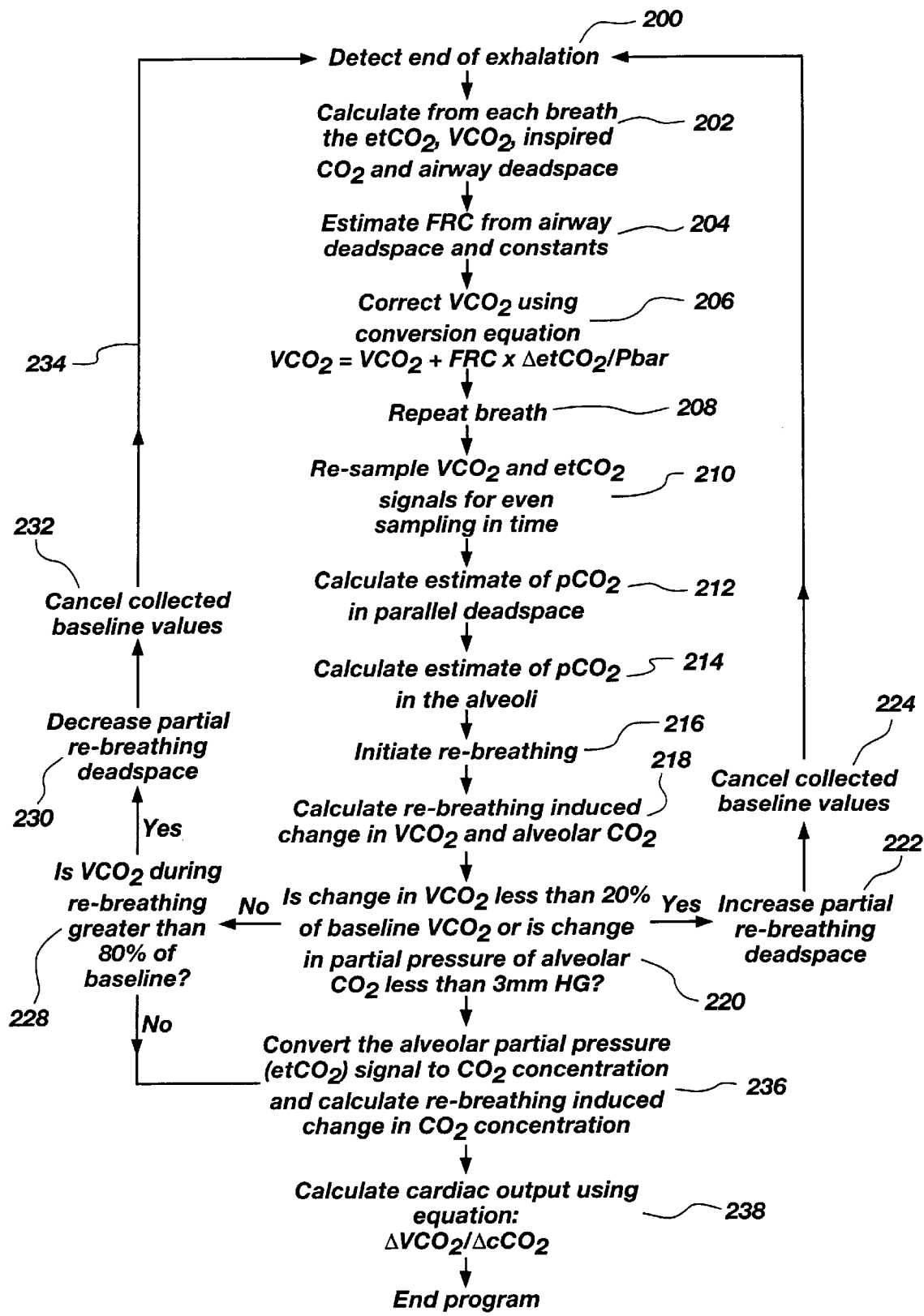
FIG. 11 is a flow diagram briefly describing the calculations made in the software program to calculate cardiac output from the measured values of normal breathing and partial re-breathing.

The operation logic of the software program is briefly illustrated in the flow chart of FIG. 11. The computer is programmed to detect the end of an exhalation 200 at which point the computer collects data from the $CO_2$ sensor and the flow meter and calculates $CO_2$, $VCO_2$, Inspired $CO_2$ and airway deadspace values 202. The program then calculates FRC, at 204, according to the equation previously noted. The program also corrects the $VCO_2$ value, at 206, in accordance with the equation previously described. At thirty second intervals (thirty seconds only being an average time, which may be adjusted higher or lower commensurate with the size of the patient), the $CO_2$ and $VCO_2$ values are recalculated, at 210, to provide an average of those values based on time, not on the variable time at which exhalation may end.

The program then calculates the estimated $pCO_2$ in the parallel deadspace 212 and calculates the estimated $pCO_2$ in the alveoli 214 using the equations previously described. At that point, a re-breathing episode is initiated 216 and a deadspace is introduced. Again, the computer collects data from the $CO_2$ sensor and the flow monitor of the apparatus and from that data, the change in $VCO_2$ and alveolar $CO_2$ induced by the introduction of the deadspace is calculated 218. If the calculated change in $VCO_2$ is less than twenty percent (20%) of the baseline $VCO_2$ or if the change in partial pressure of alveolar $CO_2$ is less than 3 mm Hg 220, then the operator is notified to increase the partial re-breathing deadspace 222 by increasing the expandable volumetric dimension of the adjustable deadspace of the apparatus. Baseline values are cancelled 224, then recalculated, as suggested by arrow 226. If, however, the change in $VCO_2$ during re-breathing is greater than 80% of baseline values 228, then the operator is notified to decrease the adjustable deadspace of the apparatus by decreasing the volumetric dimension of the adjustable deadspace 230. The baseline values are cancelled 232 and recalculated, as suggested by arrow 234. Notably, the computer may notify the operator to make the necessary changes in the adjustable deadspace or, in an alternative embodiment, the computer may signal mechanical means connected to the adjustable deadspace to increase or decrease the volumetric dimension of the deadspace automatically.

Upon proper adjustment of the adjustable deadspace and the recalculation of baseline $CO_2$, $VCO_2$, inspired $CO_2$ and airway deadspace values, the alveolar partial pressure ($etCO_2$) is converted by the software program to $CO_2$ content and the change in $CO_2$ content induced by the introduction of deadspace in the re-breathing episode is calculated 236. From those values, cardiac output is calculated 238 in accordance with the equation previously described.

All references to times of data collection assume a thirty (30) second re-breathing period. However, the actual length of time for periods of re-breathing is dependent upon the patient's size, lung capacity and cardiac output determined from previous breathing cycles. The program also controls the operation of the shunt valve or valves in the re-breathing apparatus. The valve or valves are opened based on a timer value determined by patient size, capacity and/or cardiac output.

The ventilation apparatus of the present invention provides a new and more accurate means of determining cardiac output in patients. The structure and electronic capabilities of the present invention may be modified, however, to meet the demands of the particular application. Hence, reference herein to specific details of the illustrated embodiments is by way of example and not by way of limitation. It will be apparent to those skilled in the art that many additions, deletions and modifications to the illustrated embodiments of the invention may be made without departing from the spirit and scope of the invention as defined by the following claims.

What is claimed is:

1. Apparatus for non-invasive determination of cardiac output, comprising:

an airway conduit adapted for communication with a patient's respiratory system;

an inspiratory conduit interconnected to said airway conduit;

an expiratory conduit interconnected to said airway conduit;

a volume-adjustable deadspace comprising a plurality of shunt lines positioned in fluid communication between said expiratory conduit and said inspiratory conduit, each said shunt line including a selectively actuatable shunt valve providing movement of exhaled gas between said inspiratory conduit and said expiratory conduit; and detection apparatus positioned in proximity to said airway conduit for detecting a change in concentration of at least one gas and in gas flow relating to said patient's respiratory system.

2. The apparatus of claim 1, further comprising a source of ventilation in communication with said airway conduit to provide gas to the patient.

3. Apparatus for non-invasive determination of cardiac output comprising:

an airway conduit adapted for communication with a patient's respiratory system;

an inspiratory conduit interconnected to said airway conduit;

an expiratory conduit interconnected to said airway conduit, at least one of said expiratory conduit and said inspiratory conduit including at least one volume-expandable section a volume-adjustable deadspace comprising at least one shunt line positioned in fluid communication between said expiratory conduit and said inspiratory conduit, said at least one volume-expandable section being positioned to selectively expand said volume-adjustable deadspace; and detection apparatus positioned in proximity to said airway conduit for detecting a change in concentration of at least one gas and in gas flow relating to said patient's respiratory system.

4. The apparatus of claim 3, further comprising a source of ventilation in communication with said airway conduit to provide gas to a patient.

5. The apparatus of claim 3, further comprising a plurality of shunt lines extending between said expiratory conduit and said inspiratory conduit, each said shunt line having a selectively actuatable shunt valve providing movement of exhaled gas between said inspiratory conduit and said expiratory conduit.

6. Apparatus for non-invasive determination of cardiac output, comprising:

an airway conduit adapted for communication with a patient's respiratory system;

an inspiratory conduit interconnected to said airway conduit;

an expiratory conduit interconnected to said airway conduit;

a volume-adjustable deadspace comprising a length of conduit in communication with at least said airway conduit, said length of conduit comprising a volume-expandable section; and detection apparatus positioned in proximity to said airway conduit for detecting a change in concentration of at least one gas and in gas flow relating to said patient's respiratory system.

7. The apparatus of claim 6, further comprising a valve configured for selectively directing gas through said length of conduit.

8. The apparatus of claim 6, further comprising a source of ventilation in communication with said airway conduit to provide gas to a patient.

9. The apparatus of claim 6, wherein said length of conduit further comprises an inlet, an outlet and a restrictor valve positioned therebetween in said airway conduit, and further comprising a valve positioned to selectively effect closure of a path through said volume-adjustable deadspace between said inlet and said outlet.

10. The apparatus of claim 9, further comprising a source of ventilation in communication with said airway conduit to provide gas to a patient.

11. Apparatus for non-invasive determination of cardiac output, comprising:

an airway conduit adapted for communication with a patient's respiratory system;

an inspiratory conduit interconnected to said airway conduit;

an expiratory conduit interconnected to said airway conduit;

a volume-adjustable deadspace comprising a selectively length-expandable section in communication between said airway conduit and said expiratory conduit and a selectively length-expandable section in communication between said airway conduit and said inspiratory conduit; and detection apparatus positioned in proximity to said airway conduit for detecting a change in concentration of at least one gas and in gas flow relating to said patient's respiratory system.

12. Apparatus for non-invasive determination of cardiac output comprising:

an airway conduit adapted for communication with a patient's respiratory system;

an inspiratory conduit interconnected to said airway conduit;

an expiratory conduit interconnected to said airway conduit;

a volume-adjustable deadspace comprises an expandable section of conduit in communication between said airway conduit and a source of ventilation gas; and detection apparatus positioned in proximity to said airway conduit for detecting a chance in concentration of at least one gas and in gas flow relating to said patient's respiratory system.

13. Apparatus for non-invasive determination of cardiac output, comprising:

an airway conduit adapted for communication with a patient's respiratory system;

an inspiratory conduit interconnected to said airway conduit;

an expiratory conduit interconnected to said airway conduit;

a volume-adjustable deadspace including an evacuation line connected to said expiratory conduit and a gas releasing structure for evacuating gas from said evacuation line to reduce the volume of said deadspace; and detection apparatus positioned in proximity to said airway conduit for detecting a change in concentration of at least one gas and in gas flow relating to said patient's respiratory system.

14. The apparatus of claim 13, further comprising a compliant receptacle in communication with said evacuation line and configured to receive evacuated exhaled gas.

15. Apparatus for non-invasive determination of cardiac outputs comprising;

an airway conduit adapted for communication with a patient's respiratory system;

an inspiratory conduit interconnected to said airway conduit;

an expiratory conduit interconnected to said airway conduit;

a volume-adjustable deadspace provided by a tracheal gas insufflation device; and detection apparatus positioned in proximity to said airway conduit for detecting a change in concentration of at least one gas and in gas flow relating to said patient's respiratory system.

16. Apparatus for non-invasively determining cardiac output of a patient comprising an airway conduit for contact with a patient's airway, an inspiratory conduit connected to said airway conduit and an expiratory conduit connected to said airway conduit, said expiratory conduit being structured with an evacuation line for selectively evacuating an amount of exhaled gas from said patient and a selectively-adjustable valve connected to said evacuation line for releasing an amount of exhaled gas through said evacuation line.

17. The apparatus of claim 16 further comprising an evacuation port for releasing gas, and further comprising a compliant receptacle connected thereto for receiving said exhaled gas.

18. The apparatus of claim 16 further comprising a source of ventilation in communication with said airway conduit to provide gas to a patient.

19. Apparatus for non-invasively determining cardiac output of a patient comprising an airway conduit adapted to be contacted with a patient's airway, a source of gas in communication with said airway conduit, a gas insufflation conduit extending from said source of gas to said patient's lungs and positioned in tandem with said airway conduit to directly deliver gas to a patient's lungs for insufflation thereof, a source of ventilation connected to said airway conduit for providing gas thereto, an inspiratory conduit interconnected between said source of ventilation and said airway conduit and an expiratory conduit interconnected between said source of ventilation and said airway conduit, said gas insufflation conduit and airway conduit being sized and positioned to provide an intermittent deadspace from which a patient can re-breath exhaled gas.

20. A method for non-invasively measuring cardiac output comprising:

providing ventilation apparatus for measuring pulmonary gas output of a patient, said apparatus including an airway conduit for contact with a patient's trachea, an inspiratory tube connected to said airway conduit, an expiratory tube connected to said airway conduit and a deadspace connected to said airway conduit;

placing said airway conduit in fluid communication with a patient's trachea to provide ingress and egress of air therethrough;

initiating normal breathing in the patient;

measuring the volume of gas and end-tidal gas concentration for a selected period of ventilation to establish a baseline gas concentration and gas volume output;

calculating the end-tidal concentration of gas and calculating the concentration of gas over the period of one inhalation and one exhalation;

calculating the concentration of gas during exhalation and calculating anatomic deadspace;

determining a correction value for alveolar deadspace from said calculated concentration of gas over the period of one inhalation and one exhalation;

determining a correction value for parallel deadspace from said calculated end-tidal gas concentration;

introducing a change in ventilation by directing exhaled gas from the patient into said deadspace of said ventilation apparatus for re-breathing by the patient;

measuring the change in gas volume and gas concentration during an episode of re-breathing;

repeating said normal breathing and measuring of said volume of gas and end-tidal gas concentration, and recalculating end-tidal gas concentration, gas concentration over inhalation and exhalation and gas concentration during inspiration;

redetermining said correction value for parallel deadspace; and calculating the difference between said baseline gas concentrations and volume of gas output with the detected change in gas concentration and gas volume output following re-breathing.

21. The method according to claim 20 wherein said deadspace of said ventilation apparatus is volume-adjustable, said method further comprising:

adjusting said volume-adjustable deadspace of said ventilation apparatus responsive to a perceived variance from a selected value of gas concentration per volume of gas prior to repeating said normal breathing.

22. The method according to claim 21 wherein said measured gas is $CO_2$ expelled from the lungs of said patient.

23. The method according to claim 22 wherein said adjusting of said volume-adjustable deadspace comprises expanding the volume of said deadspace responsive to a perceived value of expelled gas volume less than twenty percent of said baseline value of expelled gas volume.

24. The method according to claim 22 wherein said adjusting of said volume-adjustable deadspace comprises expanding the volume of said deadspace responsive to a perceived change in value of an alveolar gas concentration less than 3 mm Hg partial pressure.

25. The method according to claim 22 wherein said adjusting of said volume-adjustable deadspace comprises decreasing the volume of said deadspace responsive to a perceived value of greater than eighty percent of said baseline expelled gas volume.

26. The method according to claim 22 wherein said adjusting of said volume-adjustable deadspace comprises evacuating a portion of said exhaled re-breathed gas from said deadspace.

* * * * *